US006099463A

United States Patent [19]

Hockhalter

[11] Patent Number: 6,099,463

[45] Date of Patent: Aug. 8, 2000

[54] FEMALE STIMULATOR COMPRISING CLOSE-FITTING CLITORAL SUCTION CHAMBER

[76] Inventor: Robert Hockhalter, 8126 W. Evergreen La., Frankfort, Ill. 60423

[21] Appl. No.: 09/128,607

[22] Filed: Aug. 3, 1998

[51] Int. Cl.[7] ........ A61F 5/00

[52] U.S. Cl. ........ 600/38

[58] Field of Search ........ 600/38; 601/84

[56] References Cited

U.S. PATENT DOCUMENTS

| | | | |
|---|---|---|---|
| D. 320,087 | 9/1991 | Sholzberg | D24/215 |
| D. 368,140 | 3/1996 | Hopper | D24/215 |
| D. 376,650 | 12/1996 | Kain | D24/215 |
| D. 378,418 | 3/1997 | Bowker et al. | D24/215 |
| 3,114,916 | 12/1963 | Hadley | 4/110 |
| 3,362,401 | 1/1968 | Katz | 128/44 |
| 3,504,665 | 4/1970 | Bakunin et al. | 128/36 |
| 3,626,931 | 12/1971 | Bysakh | 128/32 |
| 4,033,338 | 7/1977 | Igwebike | 128/36 |
| 4,531,939 | 7/1985 | Izumi | 604/73 |
| 5,020,522 | 6/1991 | Stewart | 128/79 |
| 5,243,968 | 9/1993 | Byun | 128/40 |
| 5,470,303 | 11/1995 | Leonard et al. | 601/84 |
| 5,693,002 | 12/1997 | Tucker et al. | 600/38 |

FOREIGN PATENT DOCUMENTS 2207169 9/1972 Germany .

OTHER PUBLICATIONS

Hustler Oral Pleasure device, ©1997 Topco Sales. San Fernando, CA.

Golden Bumble vibrating suction pump clitoral stimulator, ©1997 California Exotic Novelties Inc., Chino, CA.

Pussy Pleaser suction cup, discovered May 1998, sold by Leisure Time Products, P.O. Box M827, Gary, IN 46401–0827.

Jelly Climaxer stimulator, discovered May 1998, sold by Voyages Catalog Group, P.O. Box 2709, Plattsburgh, NY 12901–0239.

*Primary Examiner*—Max Hindenburg
*Assistant Examiner*—Brian Szmal
*Attorney, Agent, or Firm*—David Pressman

[57] ABSTRACT

A female stimulation device is comprised of a tubular suction chamber sized for closely fitting around a clitoris. The suction chamber is connected to a variable partial vacuum source through a tubing. The partial vacuum source may be the mouth of a user or a mechanical device, such as a vacuum bulb or pump. The clitoris is drawn outwardly by the partial vacuum, so that it is engorged with blood to produce a sexually pleasurable sensation. The force of suction may be controlled by a check and suction release valve, which is also used to release the partial vacuum. The front end of the suction chamber is shaped to provide an air-tight but comfortable seal.

21 Claims, 2 Drawing Sheets

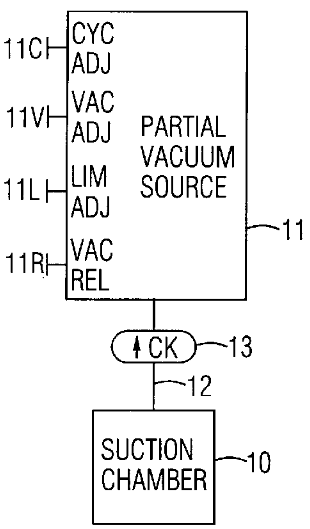
Fig. 1
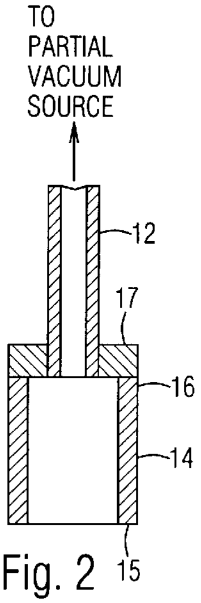
Fig. 2
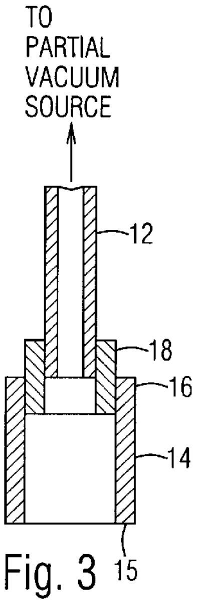
Fig. 3
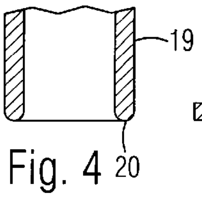
Fig. 4
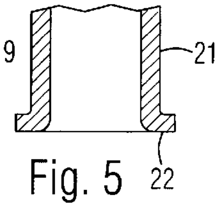
Fig. 5
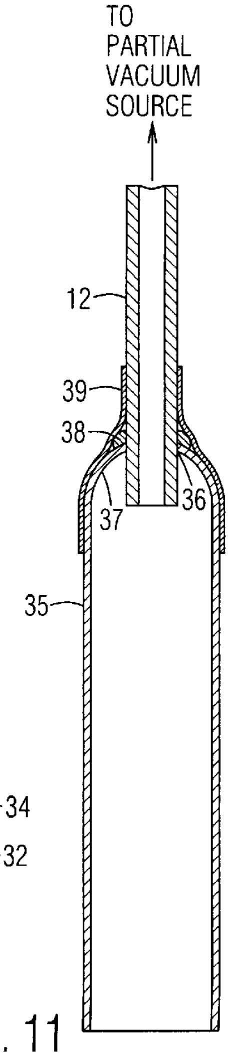
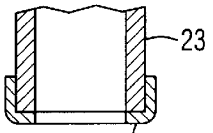
Fig. 6
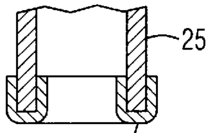
Fig. 7
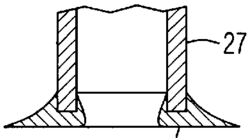
Fig. 8
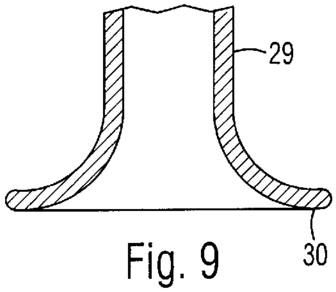
Fig. 9
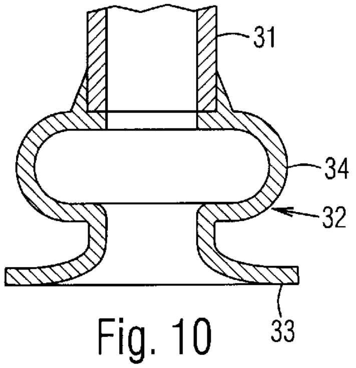
Fig. 10
Fig. 11

FEMALE STIMULATOR COMPRISING CLOSE-FITTING CLITORAL SUCTION CHAMBER

BACKGROUND OF THE INVENTION

1. Field of the Invention

This invention relates generally to sexual stimulation devices, specifically to a female stimulator.

2. Prior Art

A variety of devices have been developed for stimulating the female genitalia during masturbation or foreplay. The most common is the vibrator, which works by applying pressure, friction, and vibration to the inside or outside of the genitalia.

U.S. Pat. No. 4,033,338 to Igwebike (1977) shows a tubular device for insertion into a vagina, and cleaning its interior by suction produced with an internal motor. Being a cleaning device, it does not produce any pleasurable sensations.

U.S. Pat. No. 5,693,002 to Tucker (1997) shows a penis-worn ring with a suction cup for applying suction and vibration to a partner's vaginal area. The suction cup is about 7 cm (2.75 inches) wide, and works by alternately pressing onto and momentarily lifting the general vaginal area in concert with the stroking motion of coitus. The suction cup must be applied carefully and evenly to achieve an air-tight seal. However, the large cup covers a large and uneven genital area, and coupled with the rough motion of coitus, it is unlikely to produce any suction in practice, or if any suction is applied, it covers such a wide area as to be ineffective erotically.

Other vacuum devices similar to Tucker's have been proposed and sold, but these have the same deficiency as Tucker's.

Some vacuum devices have been available for stimulating the male genitalia, but they are not sized or shaped for use on the female genitalia. A vacuum device sold under the trademark "JOY TOY" by U.S.A. Plastics is arranged to apply suction to the female labia with a vacuum bulb. However, its cushion or seal is designed to fit over the clitoris to exclude the vacuum therefrom, so that the clitoris is not stimulated.

OBJECTS OF THE INVENTION

Accordingly the primary object of the present invention is to provide a pleasurable sexual sensation to the female clitoris. Additional objects of the invention are to provide a more heightened sensation; to be very easy and comfortable to use; to provide stimulation safely without harming the clitoris; to be usable for self-stimulation or on a partner; to be wearable under clothing for inconspicuous stimulation; and to be very simple and inexpensive to produce. Further objects of the present invention will become apparent from a consideration of the drawings and ensuing description.

SUMMARY OF THE INVENTION

A female clitoris stimulating device is comprised of a tubular suction chamber sized for closely fitting around a clitoris. The suction chamber is connected to a partial vacuum source directly, or through a tubing. The partial vacuum source may be the mouth of a user or a mechanical device, such as a vacuum bulb or pump. The clitoris is drawn outwardly by the partial vacuum, so that it is engorged with blood to produce a sexually pleasurable sensation. The force of suction may be controlled by a check valve and suction release, which is also used to release the partial vacuum. The front end of the suction chamber is shaped to provide an air-tight but comfortable seal.

BRIEF DESCRIPTION OF THE DRAWINGS

FIG. 1 is a schematic diagram of the clitoris stimulating device according to the invention.

FIG. 2 is a sectional view of a first embodiment of a suction chamber of the device.

FIG. 3 is a sectional view of a second embodiment of the suction chamber.

FIG. 4 is a sectional view of a third embodiment of the suction chamber.

FIG. 5 is a sectional view of a fourth embodiment of the suction chamber.

FIG. 6 is a sectional view of a fifth embodiment of the suction chamber.

FIG. 7 is a sectional view of a sixth embodiment of the suction chamber.

FIG. 8 is a sectional view of a seventh embodiment of the suction chamber.

FIG. 9 is a sectional view of an eighth embodiment of the suction chamber.

FIG. 10 is a sectional view of a ninth embodiment of the suction chamber.

FIG. 11 is a sectional view of a tenth embodiment of the suction chamber.

Figure 12:
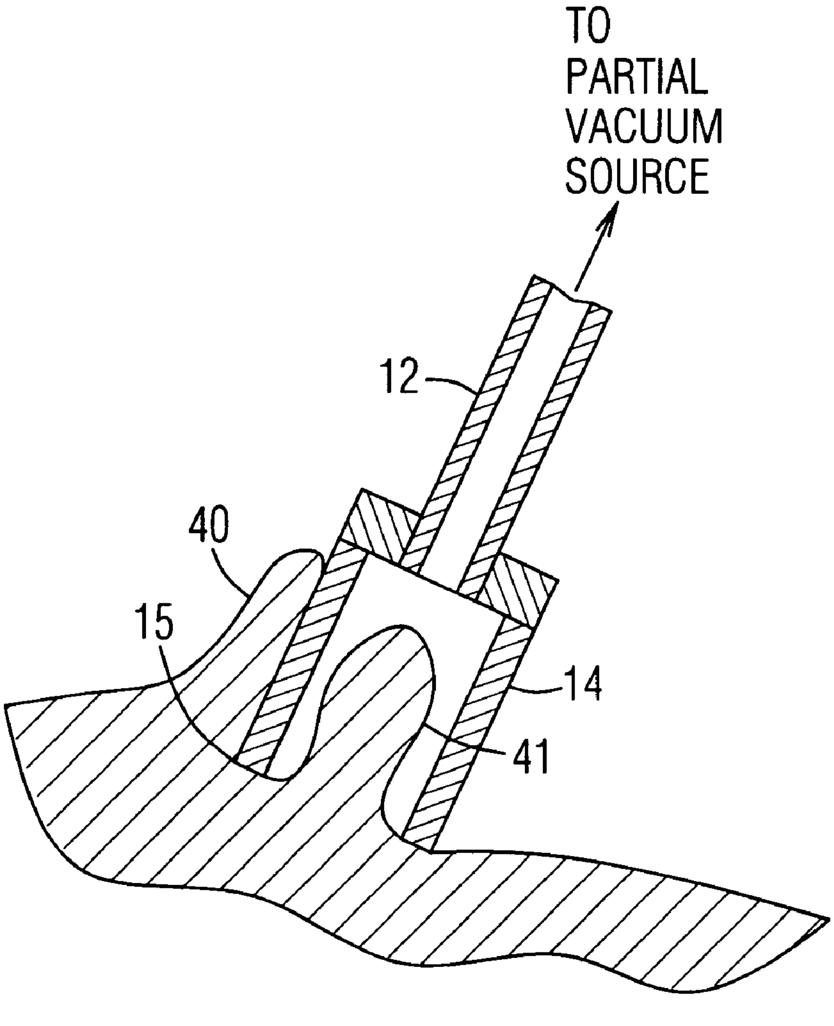
FIG. 12 is a sectional view of the device in use.

| Drawing Reference Numerals | |
|---|---|
| 10. Suction Chamber | 11. Partial Vacuum Source |
| 12. Tubing | 13. Check Valve and Vacuum Release |
| 14. Suction Chamber | 15. Front End |
| 16. Rear End | 17. Disc |
| 18. Connecting Tube | 19. Suction Chamber |
| 20. Rounded Rim | 21. Suction Chamber |
| 22. Flange | 23. Suction Chamber |
| 24. Resilient Sleeve | 25. Suction Chamber |
| 26. Resilient Cap | 27. Suction Chamber |
| 28. Resilient Flange | 29. Suction Chamber |
| 30. Bell | 31. Suction Chamber |
| 32. Suction Cup | 33. Bell |
| 34. Accordion Section | 35. Suction Chamber |
| 36. Hole | 37. Closed End |
| 38. Adhesive | 39. Heat-Shrinkable Tubing |
| 40. Clitoral Hood | 41. Clitoris |

Description—FIG. 1—Schematic Diagram

A schematic diagram of the clitoris stimulation-by-suction device is shown in FIG. 1. It includes a suction chamber 10 connected to a partial vacuum source 11 by a tubing 12. Partial vacuum source 11 may be anything that produces a variable suitable partial vacuum or suction from about 200 Torr to about 650 Torr (760 Torr=1 atmosphere). Suitable vacuum sources are the mouth of a user, a vacuum bulb, a pump, etc. A check valve and vacuum release 13 is optionally connected along tubing 12. Source 11 preferably, but not necessarily, has a vacuum adjustment control 11V, a limit adjustment 11L for limiting the vacuum to any selected value in the range, and a vacuum release 11R for releasing the vacuum after use. Also a vacuum cycle adjustment 11C may be provided for causing the vacuum pressure to cycle between its set value and no vacuum with an adjustable period of about 0.1 second to several seconds.

Description—FIG. 2—First Embodiment

As shown in FIG. 2, a first embodiment of a tubular suction chamber 14 includes a front end 15, and a rear end 16 closed with a disc 17. One end of a flexible tubing 12 is positioned through disc 17. Suction chamber 14 is sized for closely fitting around closely a clitoris (not shown), so that it is preferably about 35–50 mm long, and has an internal diameter of about 18–25 mm. The other dimensions are shown in proportion in the drawing. The internal diameter and length may be varied for accommodating smaller or larger clitorises. It may be inexpensively fabricated of acrylic or vinyl tubing, or it may be injection molded. Tubing 12 may be of any suitable length, but if the partial vacuum source is a mouth, it is preferably about 1 m long to reach from the clitoris to the mouth of the same person for self stimulation, or to the mouth of a partner for partner stimulation.

Description—FIG. 3—Second Embodiment

As shown in FIG. 3, a second embodiment of a tubular suction chamber 14 includes a front end 15, and a rear end 16 connected to tubing 12 with a short connecting tube 18 of a diameter in between those of tubular suction chamber 14 and tubing 12. The size, material, and use of the second and subsequent embodiments are similar to that of the first embodiment.

Description—FIG. 4—Third Embodiment

As shown in FIG. 4, a third embodiment of a tubular suction chamber 19 has a rounded rim 20 at its front end for comfort.

Description—FIG. 5—Fourth Embodiment

As shown in FIG. 5, a fourth embodiment of a tubular suction chamber 21 has a flange 22 at its front end for comfort and an improved seal. In lieu of the annular cap, an equivalent structure may be provided by dipping the distal end of tube 12 in a liquid rubber or plastic material of the type in which tool handles are dipped to create an insulating end cushion.

Description—FIG. 6—Fifth Embodiment

As shown in FIG. 6, a fifth embodiment of a tubular suction chamber 23 has a resilient sleeve 24 wrapped around its front end and outside wall for comfort and an improved seal.

Description—FIG. 7—Sixth Embodiment

As shown in FIG. 7, a sixth embodiment of a tubular suction chamber 25 has a resilient annular cap 26 wrapped around its tip, inside wall, and outside wall for comfort and an improved seal.

Description—FIG. 8—Seventh Embodiment

As shown in FIG. 8, a seventh embodiment of a tubular suction chamber 27 has a resilient flange 28 at its front end for comfort and an improved seal.

Description—FIG. 9—Eighth Embodiment

As shown in FIG. 9, an eighth embodiment of a tubular suction chamber 29 has a gently flared bell 30 at its front end for comfort and an improved seal.

Description—FIG. 10—Ninth Embodiment

As shown in FIG. 10, a ninth embodiment of a tubular suction chamber 31 has a suction cup 32 attached to its front end for comfort and an improved seal. Suction cup 32 includes a flared bell 33 for making contact with the genitalia, and an accordion section 34 for providing improved cushioning.

Description—FIG. 11—Tenth Embodiment

As shown in FIG. 11, a tenth embodiment of a tubular suction chamber 35 has tubing 12 inserted through a hole 36 drilled in a rear end 37. Tubing 12 is secured to tubular suction chamber 35 with adhesive 38 and a heat-shrinkable tubing 39. Tubular suction chamber 35 is preferably comprised of an inexpensive plastic floral tube, which is typically used for keeping moist the stem of a plant.

Operation—FIG. 12

The first embodiment of the device is shown in FIG. 12 to illustrate its operation. The other embodiments are operated in the same manner. Prior to use, a warm compress is preferably applied to the genital area for a few minutes to relieve tension and hypersensitivity. A suitable water-based lubricant is applied to the genitalia and the suction chamber. A clitoral hood 40 at the upper end of the genitalia is pulled back to expose a clitoris 41. The upper labium minora (not shown) is spread apart, and front end 15 of tubular suction chamber 14 is positioned around the clitoris, and seated against the skin at its base. The clitoris is thus sealed within the suction chamber. The partial vacuum source is activated to apply a partial vacuum or suction thereto. If the partial vacuum source is oral, the other end of tubing 12 is simply placed in the mouth of the user or her partner. The vacuum is applied gradually, starting at just under atmospheric pressure, about 650 Torr. The clitoris is sucked outwardly from the body, and become engorged with blood. A pleasurable sexual sensation is thus produced. The pressure is decreased until the person obtains maximum pleasure. Orally applied suction is generally strong enough for stimulation, but a mechanical partial vacuum source may be used for stronger suction (down to 200 Torr) if desired, or for isolating a partner from sexually transmitted diseases. The suction force is limited to a safe level (e.g., 200 Torr) by control 11L (FIG. 1). If the partial vacuum source is a mechanical device, the partial vacuum is also relieved by control 11R for releasing the suction chamber from the clitoris after orgasm. The risk of transmitting a sexually transmitted disease is eliminated by the use of a mechanical vacuum source. A small vacuum bulb may be used as the partial vacuum source, and II the suction chamber and tubing are small enough to be worn under clothing, so that the clitoris sucking device may be used for inconspicuous stimulation. The vacuum source may be arranged through the use of control 11C to provide a cyclic vacuum, e.g., from about 400 to about 600 Torr with a period of about 0.1 second to several seconds or more. Check valve and vacuum release 13 is optionally provided to maintain the vacuum in case source 11 fails, or so that it can be turned off after the desired vacuum level is reached.

Summary, Ramifications And Scope

Accordingly, I have provided a clitoris sucking device that provides a pleasurable sexual sensation to the female clitoris. It provides a more heightened sensation. It is very easy and comfortable to use. It provides stimulation safely without harming the clitoris. It provides stimulation without the risk of transmitting a sexually transmitted disease. It is usable for self-stimulation or on a partner. It is wearable under clothing for inconspicuous stimulation. It is also very simple and inexpensive to produce.

Although the above descriptions are specific, they should not be considered as limitations on the scope of the invention, but only as examples of the embodiments. Many other ramifications and variations are possible within the teachings of the invention. For example, a partial vacuum of any suitable pressure may be provided by any suitable partial vacuum source. The suction chamber may be fabricated of separate pieces, or molded as a single unit. The tubing may be of any length. The tubing may be eliminated if the suction chamber is directly connected to the partial vacuum source. Vibration may be transmitted to the suction chamber for providing supplemental stimulation. The tubular suction chamber may be made of hard or resilient plastic. If oral suction is used, a prophylactic barrier, such as a dental dam, may be provided on the front end of the suction chamber for protection against sexually transmitted diseases. A strap or harness may be attached to the suction chamber so that it may be held in place to allow hands-free operation. Moving air may be routed to the suction chamber to provide a cooling sensation. The suction chamber may be provided with an adapter to reduce its inner diameter for a "beginner." The end of the vacuum chamber may have an annular void inside for additional cushioning; this may be accomplished be either one- or two-piece ends. The vacuum may be provided by a venturi attached to a water source; this may be arranged to provide vibrations to the vacuum chamber. Alternatively, vibrations may be provided by a vibratory motor attached to the end. Therefore, the reader is requested to determine the scope of the invention by the appended claims and their legal equivalents, and not by the examples given.

I claim:

1. A device for stimulating the clitoris of a female pudendum, comprising:

- a tubular suction chamber having an open front end and a rear end,
- said open front end having an opening which is sized to fit closely around a clitoris of a predetermined diameter, and such that said open front end of said tubular suction chamber forms an air-tight seal when placed around said clitoris, said opening being small enough that it will not cover the vagina or any other part of said female pudendum,
- said rear end of said tubular suction chamber being connectable to a partial vacuum source so that said clitoris, but not any other part of said pudendum, will be drawn toward said rear end of said tubular suction chamber when a vacuum is applied to said rear end, so as to cause said clitoris, but not any other part of said female pudendum, to become stimulated and engorged with blood, thus producing a pleasurable, clitorally focussed, female sexual sensation.

2. The female stimulation device of claim 1, further including a check valve and vacuum release connected to said rear end of said tubular suction chamber.

3. The female stimulation device of claim 1, further including a flange around said open front end of said tubular suction chamber for an improved seal and added comfort.

4. The female stimulation device of claim 1, further including a resilient flange around said open front end of said tubular suction chamber for an improved seal and added comfort.

5. The female stimulation device of claim 1, further including a resilient sleeve around said open front end of said tubular suction chamber for an improved seal and added comfort.

6. The female stimulation device of claim 1, further including a flared bell at said open front end of said tubular suction chamber for an improved seal and added comfort.

7. The female stimulation device of claim 1, further including a suction cup attached to said rear end of said tubular suction chamber, said suction cup having a flared bell at a front end, and an accordion section at a rear end attached to said rear end of said tubular suction chamber.

8. A device for stimulating the clitoris of a female pudendum, said clitoris having a base, and skin around said base, said device comprising:

- a tubular suction chamber having an open front end and a rear end, said tubular suction chamber having an opening which is sized to fit closely around a clitoris of a predetermined diameter,
- said front end of said tubular suction chamber being sized such that said front end of said tubular suction chamber can be seated against said skin around said base of said clitoris so as to form an air-tight seal around said clitoris; but not the vagina, or any other part of said female pudendum, and
- a flexible tube having one end communicably connected to said rear end of said tubular suction chamber, another end of said flexible tube for being connected to a variable partial vacuum source for drawing said clitoris, but not any other part of said female pudendum, toward said rear end of said tubular suction chamber and causing said clitoris to become stimulated and engorged with blood, thus producing a pleasurable, clitorally focussed, female sexual sensation.

9. The female stimulation device of claim 8, further including a check valve and vacuum release connected along said flexible tube.

10. The female stimulation device of claim 8, further including a flange around said open front end of said tubular suction chamber for an improved seal and added comfort.

11. The female stimulation device of claim 8, further including a resilient flange around said open front end of said tubular suction chamber for an improved seal and added comfort.

12. The female stimulation device of claim 8, further including a resilient sleeve around said open front end of said tubular suction chamber for an improved seal and added comfort.

13. The female stimulation device of claim 8, further including a flared bell at said open front end of said tubular suction chamber for an improved seal and added comfort.

14. The female stimulation device of claim 8, further including a suction cup attached to said front end of said tubular suction chamber, said suction cup having a flared bell at a front end thereof and a bellows section at a rear end thereof, said bellows section being attached to said front end of said tubular suction chamber.

15. A device for stimulating the clitoris of a female pudendum, said clitoris having a base, and skin around said base, said device comprising:

- a tubular suction chamber having an open front end and a rear end, said tubular suction chamber having an opening which is sized to fit closely around a clitoris of a predetermined size,
- said front end of said tubular suction chamber being sized such that said front end of said tubular suction chamber can be seated against said skin around said base of said clitoris so as to form an air-tight seal around said clitoris; but not the vagina, or any other part of said female pudendum, and
- a flexible tube having one end communicably connected to said rear end of said tubular suction chamber; and
- a variable, mechanical partial vacuum source connected to another end of said flexible tube for drawing said clitoris toward said rear end of said tubular suction chamber and causing said clitoris to become stimulated and engorged with blood, thus producing a pleasurable, clitorally focussed, female sexual sensation.

16. The female stimulation device of claim 15, further including a check valve and vacuum release connected along said flexible tube.

17. The female stimulation device of claim 15, further including a vacuum adjustment control attached to said partial vacuum source for controlling suction.

18. The female stimulation device of claim 15, further including a limit adjustment attached to said partial vacuum source for limiting a partial vacuum to any selected value within a predetermined range.

19. The female stimulation device of claim 15, further including a vacuum release attached to said partial vacuum source for releasing a vacuum after use.

20. The female stimulation device of claim 15, further including a vacuum cycle adjustment attached to said partial vacuum source for causing a vacuum pressure to cycle between a set value and no vacuum.

21. The female stimulation device of claim 15, further including a suction cup attached to said front end of said tubular suction chamber, said suction cup having a flared bell at a front end thereof and a bellows section at a rear end thereof, said bellows section being attached to said front end of said tubular suction chamber.

* * * * *

UNITED STATES PATENT AND TRADEMARK OFFICE

CERTIFICATE OF CORRECTION

PATENT NO.: 6,099,463

DATED: Aug 8,2000

PATENTEE(S): Hockhalter, Robert

I t is certified that error appears in the above-identified patent and that said Letters Patent is hereby corrected as shown below:

Col. 4, line 47, delete “II”.

Signed and Sealed this

Twenty-second Day of May, 2001

*Attest:*

Nicholas P. Godici

NICHOLAS P. GODICI

*Attesting Officer* *Acting Director of the United States Patent and Trademark Office*